(12) United States Patent
Stoicescu (10) Patent No.: US 7,875,716 B2
(45) Date of Patent: Jan. 25, 2011

(54) INHIBITORS OF FOLIC ACID-DEPENDENT ENZYMES

(76) Inventor: Dan Stoicescu, Gr. Afxenthiou 5, Agios Tychonas, Limassol (CY) 4521

( * ) Notice: Subject to any disclaimer, the term of this patent is extended or adjusted under 35 U.S.C. 154(b) by 143 days.

(21) Appl. No.: 12/080,844

(22) Filed: Apr. 7, 2008

(65) Prior Publication Data

US 2008/0214550 A1 Sep. 4, 2008

Related U.S. Application Data

(62) Division of application No. 11/663,567, filed as application No. PCT/EP2006/065380 on Aug. 16, 2006.

(30) Foreign Application Priority Data

Aug. 17, 2005 (EP) .................................. 05107582

(51) Int. Cl.
C07D 475/00 (2006.01)
C07D 487/00 (2006.01)
(52) U.S. Cl. .................. 544/257; 544/258; 544/259; 544/260; 544/280
(58) Field of Classification Search ............. 514/262.1, 514/258.1; 544/257, 258, 259, 260, 280
See application file for complete search history.

(56) References Cited

U.S. PATENT DOCUMENTS

| | | | |
|---|---|---|---|
| 2,512,572 A | 6/1950 | Smith et al. | |
| 4,077,957 A | 3/1978 | Piper et al. | |
| 4,684,653 A | 8/1987 | Taylor et al. | |
| 5,344,932 A | 9/1994 | Taylor | |
| 5,698,556 A | 12/1997 | Chan | |
| 2006/0083681 A1 | 4/2006 | Purohit et al. | |
| 2007/0265444 A1* | 11/2007 | Stoicescu | 544/251 |
| 2007/0287704 A1 | 12/2007 | Dollinger et al. | |
| 2008/0153833 A1 | 6/2008 | Dollinger et al. | |

FOREIGN PATENT DOCUMENTS

| | | |
|---|---|---|
| GB | 2 070 607 A | 3/1980 |
| JP | 63-218666 | 9/1988 |
| WO | WO 91/19700 | 12/1991 |

OTHER PUBLICATIONS

Smith, M. B. Organic Synthesis, McGraw-Hill, Inc. 1994, Chapter 1.*
He, et al., Highly Enantioselective Synthesis and Potential Biological Activity of Chiral Novel Nucleoside Analogues Containing Adenine and Naturally Phenol Derivatives, Tetrahedron 65, 8505-8511 (2005).*
Office Action for U.S. Appl. No. 11/663,567 mailed Feb. 18, 2009.
Office Action for U.S. Appl. No. 12/080,842 mailed Aug. 31, 2009.
Mooney et al., "Photochemistry and Photophysics of surfactant *trans*-stilbenes in supported multilayers and films at the air-water interface[1]", *J. Am. Chem. Soc.* 106: 5659-5667 (1984).
Quinlivan et al., "Methylenetetrahydrofolate reductase 677C→T Polymorphism and folate status affect one-carbon incorporation into human DNA deoxynucleosides[1,2]", *J. Nutr.* 135: 389-396 (Mar. 2005).
Smith, "Organics synthesis: Retrosynthesis, stereochemistry and conformations" (1994).
Office Action from U.S. Appl. No. 11/663,567 dated Feb. 18, 2009.
International Search Report from PCT/EP2006/065380, mailed Feb. 23, 2007.
Boger, D. et al. "Phenyl Selenoesters as Effective Precursors of Acyl Radicals for Use in Intermolecular Alkene Addition Reactions" *Journal of Organic Chemistry*, vol. 54, Apr. 14, 1989.
Office Action from U.S. Appl. No. 11/663,567 dated Aug. 13, 2008.

* cited by examiner

*Primary Examiner*—James O Wilson
*Assistant Examiner*—Erich A Leeser
(74) *Attorney, Agent, or Firm*—Wolf, Greenfield & Sacks, P.C.

(57) ABSTRACT

The invention relates to compounds of the formula I, or pharmaceutically acceptable salts thereof:

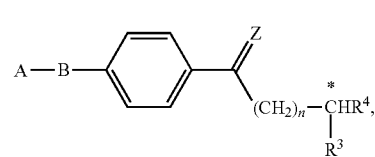

wherein:
Z=O or S;
n=1-3;
$R^3$= —$CO_2R^8$, —C(O)$SR^8$, —C(O)$NHR^8$, —C(S)$OR^8$, —C(S)$SR^8$, —C(S)$NHR^8$, —C(NH)$SR^8$ or —C(NH)$NHR^8$,
wherein $R^8$ is —H or alkyl;
$R^4$= —H, —$CH_2R^5$ or —$CH_2CH_2R^5$,
wherein $R^5$ independently has one of the meanings of $R^3$;
B= —$NR^2$—, —$CH_2NR^2$—, —$CH_2CH_2NR^2$—, —$CH_2CHR^7$— or —$CH_2O$—,
wherein $R^2$ is H or a $C_{1-3}$ alkyl, alkenyl or alkynyl group, and
$R^7$ is H or a $C_{1-3}$ alkyl or alkoxy group;
A =

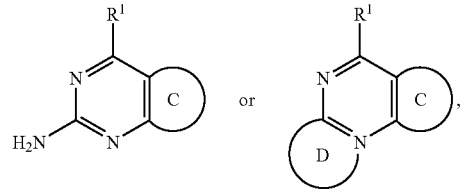

wherein $R^1$= —$NH_2$ or —OH, and C and D are each, independently, a 5- or 6-membered, substituted or unsubstituted, aromatic or non-aromatic ring which may also contain one or more heteroatoms, and C is connected to group B in any available position.

14 Claims, 1 Drawing Sheet

Figure 1

INHIBITORS OF FOLIC ACID-DEPENDENT ENZYMES

RELATED APPLICATIONS

This application is a divisional of U.S. patent application Ser. No. 11/663,567, filed Mar. 23, 2007, which claims priority to International Patent Application No. PCT/EP2006/065380, filed Aug. 16, 2006, which claims priority to European Application Serial No. EP 05107582.8, filed Aug. 17, 2005. Each of the above is incorporated herein by reference.

The present invention relates to a novel class of compounds. In particular, the present invention relates to novel compounds that inhibit enzymes whose natural substrates are folic acid or folic acid derivatives (folates), and that may be used in the treatment of diseases such as cancer.

Cancer cells replicate more rapidly than most other cells and so have a greater demand for nucleotides, the precursors of deoxyribonucleic acid (DNA) and ribonucleic acid (RNA). Since all cells do not maintain a residual store of nucleotides (except for adenosine triphosphate, ATP), they must be synthesized continually during DNA and RNA synthesis. Accordingly, the replication of cancer cells tends to be more sensitive than that of healthy cells to inhibition of nucleotide biosynthesis, and for this reason interest is increasing in chemotherapeutic agents capable of effecting such inhibition.

Nucleotides may be synthesised biologically via de novo pathways from fundamental metabolic precursors, or via salvage pathways whereby the products of nucleic acid degradation, free bases and nucleosides, are recycled. The de novo pathways are of primary interest with regard to the search for new chemotherapeutic agents.

The nucleotides 2'-deoxyadenosine-5'-monophosphate (DAMP) and 2'-deoxyguanosine-5'-monophosphate (dGMP) are both derived de novo from inosine monophosphate (IMP), which in turn is derived from 5-phosphoribosyl-1-pyrophosphate (PPRP). Two enzymes involved in the biosynthetic pathway between PPRP and IMP are GAR transformylase and AICAR transformylase. GAR transformylase converts glycinamide ribonucleotide (GAR) to formylglycinamide ribonucleotide (FGAR) using $N^{10}$-formyltetrahydrofolate, whereas AICAR transformylase uses the same compound to convert 5-aminoimidazole-4-carboxamide ribonucleotide (AICAR) to N-formylaminoimidazole-4-carboxamide ribonucleotide (FAICAR), as shown below.

The nucleotide 2'-deoxythymidine-5'-monophosphate (dTMP), on the other hand, is produced by de novo synthesis from 2'-deoxyuridine-5'-monophosphate (dUMP), a conversion catalysed by the enzyme thymidylate synthase. During the conversion, $N^5,N^{10}$-methylene-tetrahydrofolate is reduced to 7,8-dihydrofolate; the former is regenerated via tetrahydrofolate using the enzymes dihydrofolate reductase (DHFR) and serine hydroxymethyl-transferase. These processes are illustrated below.

potent chemotherapeutic agent methotrexate, which belongs to the class of "folate antagonists", and inhibits DNA synthesis by competitively antagonising dihydrofolate reductase, binding with about 100 times higher affinity than its natural substrate, thereby preventing the regeneration of tetrahydrofolate which is essential for the synthesis of dTMP. This leads to so-called "thymine-less death" in cancer cells. Methotrexate also inhibits GAR transformylase, AICAR transformylase Interference with these mechanisms has been exploited in the treatment of cancer. For example, U.S. Pat. No. 2,512,572 discloses a number of substituted pteridines including the and thymidylate synthase, albeit to a lesser degree. The structures of methotrexate and other related anti-folates are shown below.

| Compound | Structure |
|---|---|
| Methotrexate |  |

-continued

| Compound | Structure |
|---|---|
| Aminopterin | |
| Pemetrexed | |
| Lometrexol | |

U.S. Pat. No. 4,684,653 discloses compounds of the formula:

wherein $R^1$ is OH or $NH_2$, and $R^3$ is H, Me or Et, and their corresponding 5,6,7,8-tetrahydro derivatives. These compounds are disclosed to have an effect on one or more enzymes that utilize folic acid and its metabolic derivatives as a substrate.

U.S. Pat. No. 5,344,932 discloses glutamic acid derivatives of the formula:

wherein $R^5$ is H or $NH_2$, $R^4$ is H or OMe, and $R^2$ is H or a pharmaceutically acceptable cation, and discloses that they have an inhibitory effect on one or more enzymes which utilise folic acid and its metabolic derivatives as a substrate.

U.S. Pat. No. 4,077,957 discloses a method of synthesising various pteridine compounds, including:

Although such compounds have proved useful in developing new therapeutic strategies for treating cancer, there are still a number of problems associated with their use, including low efficacy, intrinsic and acquired resistance to such drugs in some patients, toxicity and adverse side effects. Consequently, there remains a need for alternative compounds that can be used in treating cancer and may address one or more of the aforementioned problems.

Accordingly, in a first aspect of the invention, there is provided a compound of the formula I, or a pharmaceutically acceptable salt thereof:

wherein:
Z=O or S;
n=1-3;

$R^3$=—$CO_2R^8$, —$C(O)SR^8$, —$C(O)NHR^8$, —$C(S)OR^8$, —$C(S)SR^8$, —$C(S)NHR^8$, —$C(NH)SR^8$ or —$C(NH)NHR^8$, wherein $R^8$ is —H or alkyl;

$R^4$=—H, —$CH_2R^5$ or —$CH_2CH_2R^5$, wherein $R^5$ independently has one of the meanings of $R^3$;

B=—$NR^2$—, —$CH_2NR^2$—, —$CH_2CH_2NR^2$—, —$CH_2CHR^7$— or —$CH_2O$—, wherein $R^2$ is H or a $C_{1-3}$ alkyl, alkenyl or alkynyl group, and $R^7$ is H or a $C_{1-3}$ alkyl or alkoxy group;

A = wherein $R^1$=—$NH_2$ or —OH,

C and D are each, independently, a 5- or 6-membered, substituted or unsubstituted, aromatic or non-aromatic ring which may also contain one or more heteroatoms, and C is connected to group B in any available position.

In a second aspect of the invention, there is provided a compound according to the invention in its first aspect, for use in therapy.

In a third aspect of the invention, there is provided a pharmaceutical composition comprising a compound according to the invention in its first or second aspects.

In a fourth aspect of the invention, there is provided the use of a compound according to the invention in its first or second aspects for the manufacture of a medicament for use in the treatment of a condition responsive to inhibition of an enzyme dependent upon folic acid or a folic acid derivative.

In a fifth aspect of the invention, there is provided the use of a compound according to the invention in its first or second aspects for the manufacture of a medicament for use in the treatment of cancer.

In a sixth aspect of the invention, there is provided a method of preparing a compound according to the invention in its first or second aspects, which comprises the step of:

(a) reacting a compound of the formula II

II wherein A is as previously defined, m is 0, 1 or 2 and X is a leaving group, with a compound of the formula III

III wherein Z, n, $R^2$, $R^3$ and $R^4$ are as previously defined;

(b) reacting a compound of the formula IV

IV wherein A is as previously defined and X is a leaving group, with a compound of the formula V

V wherein Z, n, $R^3$ and $R^4$ are as previously defined; or

(c) converting one of the following compounds VI or VII into a corresponding organometallic reagent

VII wherein A, Z, n, $R^3$, $R^4$, and $R^7$ are as previously defined, and Y is, in each case independently, a halide, and reacting said reagent with the other of compounds VI or VII.

In a seventh aspect of the invention, there is provided a method of preparing a compound according to the invention in its first or second aspects having the formula I-A or a pharmaceutically acceptable salt thereof

I-A wherein n, $R^1$, $R^3$ and $R^4$ are as previously defined, which comprises reacting a compound of the formula II-A

II-A wherein X is Cl, Br or I, with a compound of the formula III-A

III-A

In an eighth aspect of the invention, there is provided a compound of the formula III, V or VII as previously defined, except that $R^4$ is —$CH_2R^5$ or —$CH_2CH_2R^5$.

Preferred embodiments of the invention in any of its various aspects are as described below or as defined in the subclaims.

In all of the various aspects of the invention, the carbon marked C* may be asymmetric (when $R^4$ is not H) and in this event it will be appreciated that compounds of the formula I may exist in racemic form, or may be separated into their (+) or (−) enantiomers by conventional methods. In addition, other chiral centres may be present in some compounds giving rise to one or more further pairs of enantiomers. For example, a second chiral centre exists in those compounds wherein B=—$CH_2CHR^7$— wherein $R^7$ is a $C_{1-3}$ alkyl or alkoxy group. All such racemic or enantiomeric forms are intended to lie within the scope of the present invention. Furthermore, it will be understood that the compounds of formula I may exist in one or more tautomeric forms, and each of these forms are also intended to lie within the scope of the present invention.

As described in more detail hereinafter, the compounds of formula I are structural analogs of folic acid and have been found to possess activity as inhibitors of those enzymes that are dependent upon folic acid or folic acid derivatives (folates), such as dihydrofolate reductase (DHFR), at levels comparable to that of methotrexate in vitro. The compounds of formula I have also been shown to be active in inhibiting tumor growth in animal models in vivo. It is expected that the latter activity may be due to the compounds' ability to act as competitive antagonists of DHFR, although details of the mechanism are not presented here. The compounds of formula I may be used in treating cancer, as well as conditions that are responsive to inhibition of an enzyme dependent upon folic acid or a folic acid derivative.

In preferred compounds of the formula I, one or more of the following conditions are satisfied:

Z is O;
n is 1;
$R^3$ is —$CO_2R^8$ and $R^4$ is —$CH_2CH_2CO_2R^8$;
$R^8$ is —H, methyl, ethyl, n-propyl, isopropyl, n-butyl, isobutyl or tertiary butyl, preferably —H, -Me or -Et, preferably —H;
B is —$CH_2NR^2$—, —$CH_2CHR^7$— or —$CH_2O$—, preferably —$CH_2NR^2$—;
$R^2$ is —H, -Me, -Et or —$CH_2$—C≡CH, preferably H;
$R^7$ is —H, -Me, -Et or —OMe, preferably H.

In addition, preferred compounds of the formula III, V or VII display one or more of the preferred designations of Z, n, $R^2$, $R^3$, $R^4$ and/or $R^7$ set out above.

In group A in formulae I, II, IV or VI, D is preferably a 5-membered heteroaromatic ring. Preferably, A is In group A, C may be one of the following groups (points of attachment to the adjacent ring and to group B are shown):

wherein X is CH or N, and either: Y is C and $R^6$ is H, Me, Et or HCO; or Y is N and $R^6$ is a lone pair of electrons. In preferred embodiments, X and Y are both N and $R^6$ is a lone pair of electrons.

Especially preferred A groups are those of the following structures, which closely mimic those found in naturally occurring pteridines and other heterocyclic bases:

Of particular interest are the following two A groups:

Especially preferred are compounds of the formula I having the above two A groups, wherein B is —$CH_2NR^2$—, $R^2$ is —H, -Me, -Et or —$CH_2C$≡CH, Z is O, n is 1, and $R^3$ is —$CO_2R^8$, preferably any hydrolysable ester group. Individual examples of this group of compounds are set out below.

I-A1

The compounds of the formula I can be prepared by the methods of the invention from readily available and inexpensive starting materials. In the case where B is —NR²—, —CH₂NR²— or —CH₂CH₂NR²—, for example, the compounds of formula I can be prepared by coupling a compound of the formula II with a compound of the formula III. The leaving group X will generally be a halogen such as chlorine, bromine or iodine, especially bromine or iodine. This reaction is preferably performed in a dipolar aprotic solvent such as dimethyl formamide (DMF) or dimethylacetamide (DMAc). A basic catalyst such as potassium fluoride may be used, which affords a higher yield than tertiary amines or sodium bicarbonate. Where necessary, sensitive groups may be protected prior to the reaction using suitable protecting groups known in the art, and later deprotected via standard methods. For example, when R³ is H and R⁴ is CH₂CH₂CO₂H, these acid groups may be protected for instance as methyl ester groups, with subsequent deprotection by known methods such as alkaline hydrolysis with sodium hydroxide in ethanol and precipitation by addition of acid, such as glacial acetic acid. Accordingly, it will be understood that the method of the invention encompasses the reaction of compounds of the formulae II and III wherein either or both of these compounds are in a protected form.

In the case where B is —CH₂O—, the compounds of formula I may be prepared, for example, by coupling a compound of the formula IV with a compound of the formula V by a Williamson ether type reaction. In this reaction, the compound of formula V is generally converted into its aroxide ion form prior to reaction with the compound of formula IV, using a base such as NaH, for instance. X may be any suitable leaving group, in particular a halide.

In the case where B is —CH₂CHR⁷—, the compound of formula I may be prepared, for example, by coupling a compound of the formula VI with a compound of the formula VII by any known carbon-carbon bond forming reaction, especially those involving the use or formation of organometallic reagents such as Grignard reagents and lithium or copper-lithium compounds. For instance, a compound of the formula VII may be converted into its corresponding Grignard reagent or lithium cuprate reagent and reacted with a compound of the formula VI. Alternatively, a compound of the formula VI may be converted into its corresponding Grignard reagent or lithium cuprate reagent and reacted with a compound of the formula VII. Once again, suitable protecting groups for any reactive substituent groups will be well-known to those skilled in the art.

The intermediates II to VII may be prepared by conventional methods. By way of illustration, compounds of the formula III, V or VII may be prepared by reacting a compound of the formula with a compound of the formula wherein B' is —NHR², —OH or —CHYR⁷ and X is a leaving group, in the presence of a base. This may be followed by removal of the cyano group by hydrolysis and decarboxylation, with the use of suitable protecting groups where necessary.

Compounds of formula I have an inhibitory effect on one or more enzymes which utilize folic acid, and in particular metabolic derivatives of folic acid as a substrate. These enzymes include GAR transformylase, AICAR transformylase, dihydrofolate reductase and thymidylate synthase. The compounds appear to be particularly active as inhibitors of dihydrofolate reductase. They can be used, alone or in combination, to treat neoplasms which in the past have been treated with methotrexate, including choricarinoma, leukaemia, adenocarcinoma of the female breast, epidermid cancers of the head and neck, squamous or small-cell lung cancer, and various lymphosarcomas. Although not wishing to be limited by theory, it is believed that the modified ketomethylenic or thioketomethylenic side chain of the compounds of formula I leads to a lower renal toxicity compared with methotrexate. Inactivation due to hydrolysis is minimal due to the lower lability of the ketomethylenic or thioketomethylenic group, allowing a longer half-life. In addition, compounds of the formula I exhibit improved physico-chemical characteristics compared with those of the prior art.

As discussed above, primary interest in the compounds of the invention relates to their use in the treatment of cancer, since cancerous cells replicate more rapidly than healthy cells and so have a greater demand for nucleotides. The therapeutic utility of the compounds of the invention extends further than this, however, since all fast-growing cells have a similar high demand for nucleotides. For example, methotrexate has been used in the treatment of psoriasis and mycosis fungoides, and in inducing miscarriage in patients with ectopic pregnancy. Methotrexate has also been used in the treatment of rheumatoid arthritis, although the mechanism of action in this instance is not fully understood.

The compounds may be administered either orally or preferably parenterally, alone or in combination with other antineoplastic agents or with other therapeutic agents, such as steroids, to a mammal, preferably a human, suffering from neoplasm and in need of treatment. Parenteral routes of administration include intramuscular, intrathecal, intravenous or intra-arterial.

BRIEF DESCRIPTION OF THE DRAWINGS

In order that the invention may be more fully understood, it will now be described by way of example only with reference to the accompanying drawing, wherein.

The following examples are intended to demonstrate the invention but are not intended to limit the invention in any manner.

EXAMPLE 1

Synthesis of Compound 3

Source of Starting Materials 3-chloropropanoyl chloride and ethyl cyanoacetate were obtained commercially from Sigma-Aldrich Company Ltd., The Old Brickyard, New Road, Gillingham, Dorset SP8 4XT, United Kingdom, or synthesised by standard methods. α-bromo-p-nitro-acetophenone 7 was obtained by bromination of p-nitroacetophenone with bromine in tetrahydrofuran (THF). 2,4-diamino-6-bromomethylpteridine 2 was obtained by standard methods (see, for example, U.S. Pat. No. 4,077,957 and U.S. Pat. No. 4,224,446).

Step A

Synthesis of Compound 6

3-chloropropanoyl chloride was esterified with ethanol in the presence of pyridine or triethylacetate to produce ethyl 3-chloropropionate 5. The latter was condensed with ethyl cyanoacetate according to the procedure of L. Ruzicka et. al., Helv. Chim. Acta 17, 183-200 (1934), CA 28:2584, or Koelsch, C. F., J. Am. Chem. 65, 2458-9 (1943), to form diethyl α-cyanoglutarate 6. $^1$H-NMR confirmed the expected structure. GC: 97% purity.

Step B

Synthesis of Compound 8

175 g (0.71 mmol) α-bromo-p-nitro-acetophenone 7 was added in portions at 0-5° C. to a suspension of 175 g (0.82 mmol) diethyl α-cyanoglutarate 6 and 175 g (3 mmol) KF in 500 ml DMF. The reaction was monitored by thin layer chromatography (TLC). After 4 hours, the reaction mixture was suspended in 2 l of water containing 0.1% acetic acid at pH 5. After decanting the water, the gummy precipitate was washed with water (2×750 ml) then triturated with 300 ml methanol. When crystallisation was complete, the precipitate was filtered and washed successively with an excess of methanol and ether, affording 210 g of compound 8, a yellow solid with m.p. 92.1° C. (Yield 68%) After chromatography on silica gel (50:50:5 benzene-cyclohexane-ethanol) the product had m.p. 99.7° C. TLC on silica gel plates (5:1:3:10:0.1 benzene-ethanol-cyclohexane-petroleum ether-AcOH) showed a single spot with Rf (retention factor) 0.38. HPLC: 97% purity.

Step C

Synthesis of Compound 9

30 g (0.08 mmol) compound 8 was dissolved in 400 ml methanol and hydrogenated in a hydrogenation flask at room temperature in the presence of 6 g 20% Pd/C catalyst. The theoretical volume of hydrogen (c. 6200 ml; 0.28 mmol) was absorbed in 1 hour (TLC control). The platinum catalyst was filtered and the methanol was evaporated. The crude product obtained solidified on drying in vacuo, resulting in 27.6 g compound 9, a yellow solid (yield 99%) which was used without further purification in the conversion to crude compound 10 described below. The purity was acceptable by TLC analysis. TLC (4:1 chloroform-methanol) showed a single spot, Rf 0.5 (characteristic reaction with 4-dimethylamino benzaldehyde). The HCl salt was isolated after reflux in HCl. LC-MS and $^1$-H NMR confirmed the expected structure; HPLC: 99% purity.

Step D

Synthesis of Compound 10

A solution of 52.2 g (0.15 mmol) intermediate 9 in 1000 ml methanol was prepared. 188 ml 6N NaOH was added dropwise at room temperature for 1 hour and the solution was allowed to stand for 12 hours. The reaction mixture was then diluted with 300 ml water and concentrated under high vacuum. 700 ml 37% HCl was added to the residue and the resulting mixture was heated to reflux for 4 hours. The mixture obtained was diluted with 1.5 l methanol and the NaCl precipitate was removed by filtration. The filtrate was used in step E. A small amount of diacid 10 was isolated before dilution, by filtering the suspension and washing the precipitate successively with an excess of water, acetone and ether. TLC (4:1 chloroform-methanol) showed a single spot, Rf 0.26.

Step E

Synthesis of Compound 1

The methanolic solution of the dicarboxylic acid 10 obtained in step D was cooled at 0-5° C. and 100 ml thionyl chloride was added dropwise. The reaction mixture was stirred under reflux for 3 hours, then cooled to room temperature and the solvent was evaporated off. The precipitate obtained was filtered and washed with ether, resulting in 27 g compound 1 (yield 63%), a solid with m.p. 115-116° C. After recrystallisation from tetrahydrofuran, 17.5 g white crystals of 1 were obtained having m.p. 116-117° C. TLC (4:1 chloroform-methanol) showed a single spot, Rf 0.73. UV spectra: 234, 319 nm (MeOH). $^1$H NMR spectra: 2.0 (2H, m, C$\underline{H}_2$CH$_2$COOCH$_3$), 2.5 (2H, t, CH$_2$C$\underline{H}_2$COOCH$_3$), 3.1 (2H, m, COC$\underline{H}_2$), 3.5 (1H, m, COCH$_2$C$\underline{H}$), 3.75 (6H, s, COOC$\underline{H}_3$), 7.6-8.0 (4H, m, C$\underline{H}$ arom.). HPLC: 99% purity.

Step F

Synthesis of N-[4-[[2,4-diamino-6-pteridinyl)methyl]amino]benzoyl] pseudoglutamic ester (Compound 3)

A mixture of 7 g (27.4 mmol) 2,4-diamino-6-bromomethylpteridine 2 and 7 g (23.4 mmol) dimethyl N-[4-methylamino)benzoyl]pseudogluamate 1 in 70 ml N,N-dimethylacetamide was stirred for 30 minutes at 70° C. then allowed to stand at room temperature overnight protected from light, then heated again for 10 minutes to 100° C. The reaction was controlled by TLC. After cooling, the reaction mixture was poured into water acidified with AcOH at pH 4 (1000 ml). The dark-yellow precipitate that formed was filtered and washed three times with water and allowed to air dry. 2.6 g orange-yellow product 3 was obtained, m.p. 200-210° C. The filtrate was treated with 10% $NaHCO_3$ and the precipitate formed was separated in the same manner, resulting in a second fraction of dimethyl ester 3 (2 g). Total yield: 36%. TLC (4:1 chloroform-methanol) showed a single spot, Rf 0.48. UV Spectra: 210, 242, 332 (0.1 N HCl); 238, 335 (MeOH).

EXAMPLE 2

Synthesis of N-[4-[[2,4-diamino-6-pteridinyl)methyl]amino]benzoyl] pseudoglutamic acid (Compound 4)

1 g (2.1 mmol) dimethyl ester 3 was added in portions to a solution of 10 ml 2N NaOH and 25 ml ethanol, and the mixture was stirred at room temperature for 4 hours. The precipitate formed was filtered and dissolved in distilled water. The alkaline solution was treated with charcoal, filtered and the pH was adjusted to 4.5 with 10% AcOH. The precipitate was filtered and washed with water at pH 4.5, then with acetone, resulting in 0.8 g compound 4 (yield 85%). The product, a brown solid, was purified by preparative HPTLC (High Performance Thin Layer Chromatography). After elution with 50:50:5 $CH_3CN$—$H_2O$—$NH_4OH$, the diacid was extracted from silica gel with 100 ml NaOH solution at pH 8. The water was removed by freeze-drying. TLC (7:2:1 $CH_3CN$—$H_2O$—$NH_4OH$) showed a single spot, Rf 0.80. Mass spectrum: m/z 120 (M+, 100%). IR spectra (KBr): 1651 (COCH), 1594 (C=C), 1563, 1403 (C=O acid), 1176 (C—O), 823 (CH). UV spectra: 242, 332 nm (0.1 N HCl); 232, 259, 325 nm (0.1 N NaOH); 229, 262, 318 (MeOH). $^1$H NMR: 1.6 (3H, m, CH—CH$_2$), 2.2 (2H, t, CH$_2$CH$_2$COOH), 2.9 (2H, m, COCH$_2$), 4.6 (2H, s, CH$_2$NH), 6.8-7.8 (4H, m, C H arom.), 9 (1H, s, 7-CH). HPLC: 97% purity.

Other compounds of formula I can be produced by adapting the procedures set out above in an appropriate manner. For example, intermediate 1 and analogous compounds can be converted to their corresponding N-methyl derivatives by reaction with formaldehyde and sodium cyanoborohydride. Intermediate 6 can also be produced by reacting ethyl cyanoacetate with ethyl acrylate according to standard procedures.

EXAMPLE 3

In Vitro Inhibition of DHFR

The ability of compounds of formula I to inhibit dihydrofolate reductase (DHFR) in vitro was measured using a standard DHFR enzyme inhibition assay. DHFR enzyme was purified from rat livers or the commercially available DHFR was used, this being produced by recombinant expression in E. coli. Assays of enzyme activity were performed at 37° C. by monitoring changes in UV absorbance at 340 nm of a solution containing 50 mM N-tris(hydroxymethyl)methyl-2-aminoethanesulfonic acid (pH 7.0), 1 mM EDTA, 75 μM 2-mercaptoethanol, 0.1% bovine serum albumin, 20 μM dihydrofolate, and 100 μM NADPH. Reactions were initiated by adding dihydrofolate. Each titration of the inhibitor was performed twice, and mean DHFR activity was plotted against inhibitor concentration to obtain $IC_{50}$ values. The ratio of $IC_{50(Compound)}/IC_{50(MTX)}$ was designated relative $IC_{50}$ and the results of one representative experiment (out of 5 experiments) for compounds 438 and 497 relative to methotrexate (MTX) are shown in Table 1. The results obtained overall suggest that most compounds of formula I tested possessed an in vitro potency similar to that of MTX.

TABLE 1

| Compound | Chemical formula | Relative $IC_{50}$ |
|---|---|---|
| MTX | | 1 |
| 438 | Compound 4, $R^3$ = H | 12.5 |
| 497 | Compound 4 | 0.75 |

Figure 1:
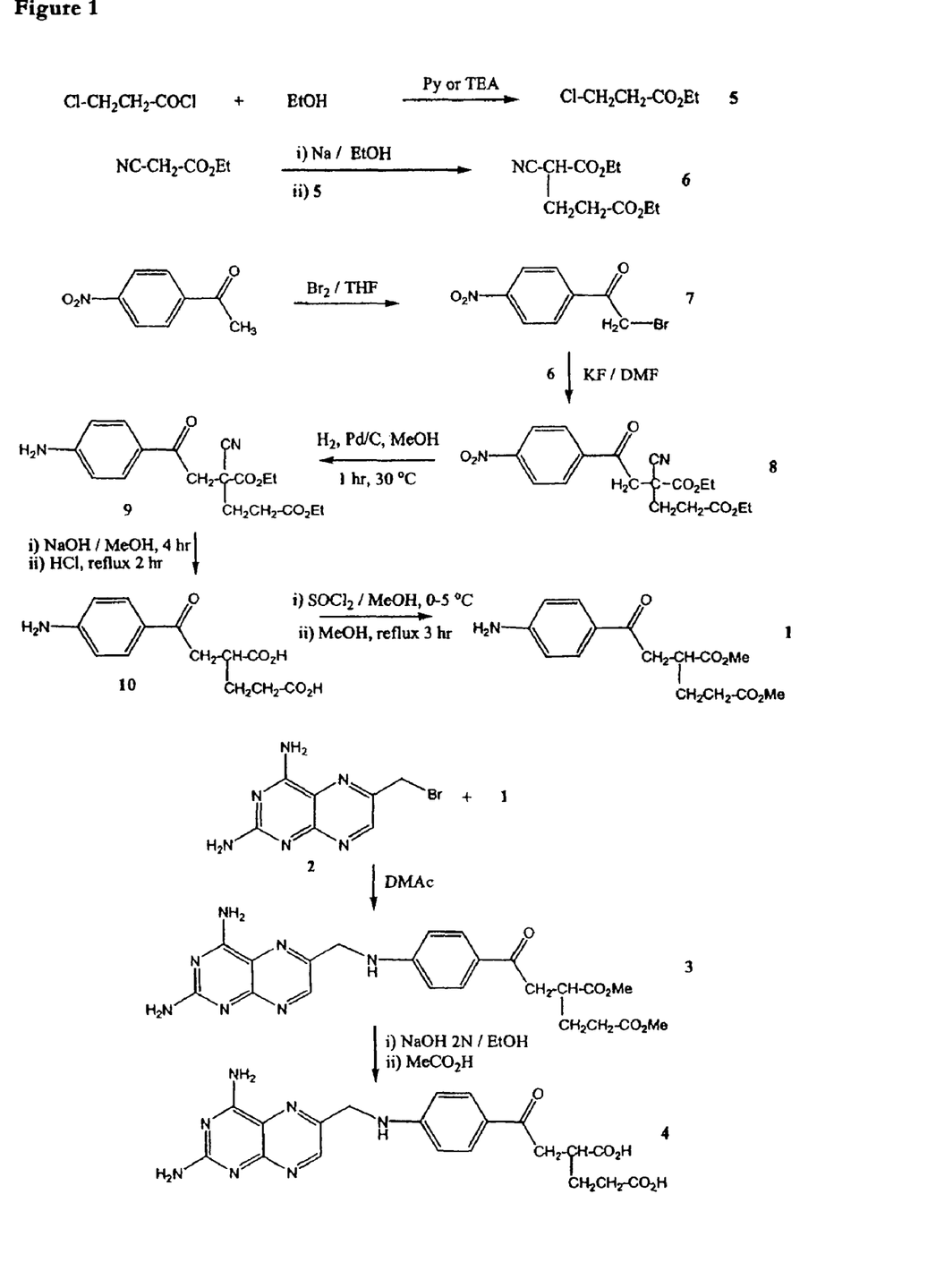
FIG. 1 is a schematic representation of the total synthesis of two compounds according to the present invention (compounds 3 and 4), as described in detail below in Examples 1 and 2.

N.B. Compound 438 has the same structure as compound 4 in FIG. 1 except that $R^3$ (—$CH_2CH_2CO_2H$) is replaced by H.

EXAMPLE 4

In Vitro Cytotoxicity

The cytotoxicity of compounds of formula I against a number of tumor cell lines (CCRF-CEM, HepG2, HeLa, KB, L1210, A549 and COLO205) was assayed by measuring cell viability at different time points following drug addition up to 72 hours, and compared with the corresponding cytotoxicity of methotrexate and pemetrexed (obtained as Alimta®). The compounds of formula I demonstrated potent inhibitory effects against growth of all the cell lines tested, with the strongest inhibitory effects being seen against the L1210 cell line. Compared with methotrexate and pemetrexed, the compounds of formula I exhibited similar or stronger inhibitory effects against all the cell lines, and in some cases the onset of cytotoxicity was more rapid. Further, compounds of formula I wherein B=—CH$_2$NH— were found to be particularly cytotoxic.

Cytotoxicity was not reversed by addition of purines, such as hypoxanthine, or by addition of aminoimidazole carboxamide (up to very high concentration), but was reversed by addition of leucovorin, indicating cytotoxicity was due to antagonism of a folate-related mechanism. Consistent with a proposed mechanism of action in which DHFR is the main target, the addition of thymidine reversed cytotoxicity induced by the compounds of formula I only at high concentrations. These effects indicate specific inhibition of de novo purine synthesis and a less significant inhibition of the thymidylate cycle, however more pronounced than in the case of methotrexate. The compounds of formula I also inhibited glycinamide ribonucleotide transformylase in a comparable concentration range to methotrexate.

EXAMPLE 5

Tumor Inhibition in Animal Models In Vivo

The ability of compounds of formula I to inhibit tumor growth in mice was tested as follows. $5 \times 10^6$ L1210 cells were injected subcutaneously in the axillary region of DBA/2 mice (groups of 8 mice/treatment). Following intraperitoneal administration of saline solution only or saline solution containing a compound of formula I the length and width of the control tumor (receiving only saline) was measured at the indicated time and compared to those of animals receiving test compound to calculate the percentage of inhibition. Intraperitoneal administration of a saline solution containing the test compound, daily for 6 days, led to 60% tumor-free long term survivors (tumor weight zero). Median survival times for saline-treated control animals and animals receiving Compound 4 (0.5 mg/kg) were 6.7 and 15.6 days, respectively. Oral administration of the compound required a higher dosage of the inhibitor and led to a less-marked, but still significant reduction of the tumor weight and 25% long-term survivors as compared with the saline-treated control group.

Compounds of formula I were also active in vivo against the carcinoma W256 (TGI=28%), most likely due to the higher solubility and thus passive transport into the tumor compared with other anti-folate agents. Median survival times for saline-treated control animals and animals receiving Compound 4 (1 mg/kg) intraperitoneally in the Walker-256 rat tumor model were 22.5 and >46.3 days, respectively.

The tumor evolution was measured following different treatment regimes and results are summarized in Table 2.

TABLE 2

Effect of various concentration of Compound 4 in a rat tumor model

| Group | Treatment | No. animals surviving at day 30 days post-transplant | Tumor volume (cm³) ± SE |
|---|---|---|---|
| 1 | Saline Control | 2/10 | 37.3 ± 0.3 |
| 2 | 0.5 mg/kg - 3 doses every 4 days | 9/10 | 13.4 ± 3.07 |
| 3 | 0.25 mg/kg - 3 doses every 4 days | 8/10 | 23 ± 3.5 |
| 4 | 0.1 mg/kg - 5 doses every day | 10/10 | 14.5 ± 3.8 |
| 5 | 1 mg/kg - one dose | 8/10 | 17.1 ± 3.3 |

The invention claimed is:

1. A method of preparing a compound, which comprises the step of:

reacting a compound of the formula II

A-(CH$_2$)$_m$—X  II wherein A is wherein R$^1$=—NH$_2$ or —OH, C and D are each, independently, a 5- or 6-membered, substituted or unsubstituted, aromatic or non-aromatic ring which may also contain one or more heteroatoms, m is 0, 1 or 2 and X is a leaving group, with a compound of the formula III wherein Z is O or S; n is 1-3; R$^2$ is H or a C$_{1-3}$ alkyl, alkenyl or alkynyl group; R$^3$ is —CO$_2$R$^8$, —C(O)SR$^8$, —C(O)NHR$^8$, —C(S)OR$^8$, —C(S)SR$^8$, —C(S)NHR$^8$, —C(NH)SR$^8$ or —C(NH)NHR$^8$, wherein R$^8$ is —H or alkyl; and R$^4$ is —H, —CH$_2$R$^5$ or —CH$_2$CH$_2$R$^5$, wherein R$^5$ independently has one of the meanings of R$^3$, to produce a compound of formula I:

wherein:
Z=O or S;
n=1-3;
R$^3$=—CO$_2$R$^8$, —C(O)SR$^8$, —C(O)NHR$^8$, —C(S)OR$^8$, —C(S)SR$^8$, —C(S)NHR$^8$, —C(NH)SR$^8$ or —C(NH)NHR$^8$,
wherein R$^8$ is —H or alkyl;
R$^4$=—H, —CH$_2$R$^5$ or —CH$_2$CH$_2$R$^5$,
wherein R$^5$ independently has one of the meanings of R$^3$;
B=—NR$^2$—, —CH$_2$NR$^2$—, —CH$_2$CHR$^7$— or —CH$_2$O—,
wherein R$^2$ is H or a C$_{1-3}$ alkyl, alkenyl or alkynyl group, and
R$^7$ is H or a C$_{1-3}$ alkyl or alkoxy group;
A= wherein R$^1$=—NH$_2$ or —OH,
C and D are each, independently, a 5- or 6-membered, substituted or unsubstituted, aromatic or non-aromatic ring which may also contain one or more heteroatoms, and C is connected to group B in any available position.

2. A method as claimed in claim 1, wherein Z is O.

3. A method as claimed in claim 1, wherein n is 1.

4. A method as claimed in claim 1, wherein R$^8$ is —H, methyl, ethyl, n-propyl, isopropyl, n-butyl, isobutyl or tertiary butyl.

5. A method as claimed in claim 1, wherein R$^3$ is —CO$_2$R$^8$ and R$^4$ is —CH$_2$CH$_2$CO$_2$R$^8$.

6. A method as claimed in claim 5, wherein R$^8$ is H, methyl or ethyl.

7. A method as claimed in claim 1, wherein R$^2$ is —H, -Me, -Et or —CH$_2$C≡CH.

8. A method as claimed in claim 1, wherein D is a 5-membered aromatic ring.

9. A method as claimed in claim 1, wherein A is

10. A method as claimed in claim 1, wherein C is:

wherein X is CH or N, and either:
Y is C and $R^6$ is H, Me, Et or HCO; or
Y is N and $R^6$ is a lone pair of electrons.

11. A method as claimed in claim 10, wherein A is of the formula A-i or A-ii:

12. A method as claimed in claim 11, wherein A is of the formula A-i-1 or A-i-1:

13. A method as claimed in claim 12, wherein $R^2$ is —H, -Me, -Et or —CH$_2$C≡CH; Z is O; n is 1; and $R^3$ is —CO$_2$R$^8$.

14. A method as claimed in claim 11, wherein $R^2$ is —H, -Me, -Et or —CH$_2$C≡CH; Z is O; n is 1; $R^3$ is —CO$_2$R$^8$; $R^4$ is —H or —CH$_2$CH$_2$CO$_2$R$^8$; $R^8$ is independently —H, -Me or -Et; if A is A-i and Y is C, $R^6$ is —H; and if A is A-ii, $R^1$ is —OH.

* * * * *